(12) United States Patent
Tsao

(10) Patent No.: US 7,588,690 B1
(45) Date of Patent: Sep. 15, 2009

(54) METHOD OF IODIDE REMOVAL

(75) Inventor: Hsiang Wei Tsao, West Chester, PA (US)

(73) Assignee: The Purolite Company, Bala Cynwyd, PA (US)

( * ) Notice: Subject to any disclaimer, the term of this patent is extended or adjusted under 35 U.S.C. 154(b) by 0 days.

(21) Appl. No.: 12/368,886

(22) Filed: Feb. 10, 2009

(51) Int. Cl.
*C02F 1/42* (2006.01)

(52) U.S. Cl. .................................... 210/688

(58) Field of Classification Search ............... 210/688
See application file for complete search history.

(56) References Cited

U.S. PATENT DOCUMENTS

| | | | |
|---|---|---|---|
| 3,769,329 A | 10/1973 | Paulik | |
| 4,615,806 A * | 10/1986 | Hilton | 210/690 |
| 5,001,259 A | 3/1991 | Smith et al. | |
| 5,139,981 A | 8/1992 | Kurland | |
| 5,220,058 A * | 6/1993 | Fish et al. | 562/608 |
| 5,227,524 A | 7/1993 | Jones | |
| 5,300,685 A * | 4/1994 | Scates et al. | 562/608 |
| 5,416,237 A | 5/1995 | Aubigne et al. | |
| 5,466,876 A * | 11/1995 | McClarron et al. | 562/608 |
| 5,561,168 A * | 10/1996 | Fish et al. | 521/33 |
| RE35,615 E * | 9/1997 | Jones et al. | 562/608 |
| 6,007,724 A * | 12/1999 | Kulprathipanja et al. | 210/670 |
| 6,017,969 A | 1/2000 | Jones et al. | |
| 6,197,997 B1 | 3/2001 | Carey et al. | |
| 6,211,408 B1 * | 4/2001 | Hilton | 562/608 |
| 6,657,078 B2 | 12/2003 | Scates et al. | |

FOREIGN PATENT DOCUMENTS

| | | |
|---|---|---|
| EP | 01611874 | 1/2006 |
| JP | 09291058 | 11/1997 |
| WO | WO-2008/003446 | 1/2008 |

* cited by examiner

*Primary Examiner*—Chester T Barry
(74) *Attorney, Agent, or Firm*—Darby & Darby P.C.

(57) ABSTRACT

The present invention provides a method of reducing the concentration of an iodide compound using an ion exchange resin. The ion exchange resin is a macroporous resin having sulfur functional groups exchanged with silver, a dry weight capacity of at least 5.0 eq/kg, a mean pore diameter ($D_{50}$) of about 400-800 Å, a pore volume of about 0.4-0.6 ml/g, and a surface area of about 20-40 $m^2$/g.

22 Claims, No Drawings

METHOD OF IODIDE REMOVAL

FIELD OF THE INVENTION

The present invention relates generally to resins and their use in aqueous and non-aqueous solvent applications, and in particular to the use of metal loaded ion exchange resins for the removal of iodide-containing compounds from an acetic acid or organic solvent process.

BACKGROUND OF THE INVENTION

Acetic acid and acetic anhydride are used for a variety of applications including the production of vinyl acetate, ester production, the formation of vinegar, and as a solvent. Acetic acid is generally produced by the carbonylation of methanol and/or methyl acetate in the presence of a catalyst containing both rhodium and iodide.

However, even after distillation, the acetic acid or acetic anhydride contains a small amount of iodide impurities. This is problematic particularly because even a small amount of iodide will reduce the lifetime of catalysts in downstream processes. For example, the majority of acetic acid produced is used in the production of vinyl acetate and cellulose acetate by processes using sensitive, expensive catalysts containing metals such as gold and palladium. Since halides, especially iodide compounds deactivate or "poison" gold and palladium catalysts, starting materials that are essentially halide-free are preferred.

Even after extensive purification, carbonylation reaction products typically contain contaminants from the original halide compounds added to the reaction medium as a promoter prior to the carbonylation reaction and new halide compounds generated during the carbonylation reaction. While the exact composition of these impurities is unknown, the impurities comprise a mixture of hydrogen iodide, alkyl iodides such as methyl iodide and hexyl iodide, and iodide salts. Other iodide compounds, including aromatic iodides, may also be present in the mixture.

The industry standard for halide contaminants in acetic acid is 10 parts per billion (ppb) or less. However, poisoning effects on precious metal catalyst are generally cumulative and irreversible as in the case of iodide contamination of catalysts for vinyl acetate production. Consequently, the removal of as much iodide contamination as reasonably possible is desired. Further, since all halide contaminants (e.g., HI, $CH_3I$, $C_6H_{13}I$, and aromatic iodides) will poison downstream catalysts, all iodide contaminants, not just the short chain aliphatic iodides, should be removed.

There are a number of resins used in acetic acid iodide purification. Most of these resins contain iodine-reactive metals such as silver, mercury, copper, lead, thallium, palladium or combinations of these metals known to react with iodine-containing compounds to form insoluble complexes. For example, in U.S. Pat. No. 4,615,806, the removal of these impurities is achieved with a macroreticulated strong acid cation-exchange resin which is stable in the organic medium and has at least one percent of its active sites converted to the silver or mercury form, presumably by cation-exchange.

Other resins, including macroreticulated silver-exchanged resins are described in U.S. Pat. Nos. 5,139,981; 5,220,058; 5,227,524; 5,300,685; 5,416,237; RE35615; 6,017,969; 6,197,997; 6,657,078. WO 2008/03446 and JP 09 291058 describe silver-exchange resins having specific particle and pore size. These resins and methods are each directed to the removal of iodide compounds. However, there is need for resins having a greater effectiveness and/or a longer life for use in removing iodide contaminants from solvents or solutions.

SUMMARY OF THE INVENTION

Now, high performance resins loaded with silver have been formed for the removal of iodides in processes such as acetic acid and organic solvents.

Thus, one aspect of the present invention is a method of reducing the concentration of an iodide compound in a liquid comprising contacting the liquid with a resin, wherein the resin comprises a strong acid macroporous resin having
at least 1% of the acid functional groups exchanged with silver,
a dry weight capacity of at least 5.0 eq/kg,
a mean pore diameter ($D_{50}$) of about 400-800 Å,
a pore volume of about 0.4-0.6 ml/g, and
a surface area of about 20-40 $m^2$/g.

In one embodiment of the present invention the resin has a volume capacity of at least 1.40 eq/l. In another embodiment of the present invention, the resin has a dry weight capacity is at least 5.1 eq/kg, at least 5.2 eq/kg, at least 5.3 eq/kg, or at least 5.4 eq/kg.

In one embodiment of the present invention the resin has a mean pore diameter ($D_{50}$) of at least 500 Å, or, in another embodiment, about 500-700 Å.

In one embodiment of the present invention, the silver loading is between 1 and 37% based on dry-weight resin base. In another embodiment, the silver loading is between 6 and 36%, and in yet another embodiment, the silver loading is between 20 and 32 percent.

In one embodiment of the present invention, the resin polymer comprises approximately 70 and 92% polystyrene and approximately 8-30% divinylbenzene. In another embodiment, the resin polymer comprises approximately 75-85% polystyrene and approximately 15-25% divinylbenzene.

The method of the present invention can be used to reduce the concentration of one or more $C_1$-$C_{12}$ alkyl iodides or, in another embodiment, more particularly one or more $C_1$-$C_8$ alkyl iodides. In one embodiment, the method preferentially removes $C_6$-$C_{12}$ alkyl iodides. The method as described herein can reduce the concentration of the iodide compounds to less than about 1 ppb, less than about 300 ppt, less than about 100 ppt, or less than about 30 ppt.

In one embodiment of the present invention, the term contacting comprises flowing the liquid through a packed bed comprising the macroporous resin. In one embodiment, the flow rate is 5 to 15 bed volumes per hour.

In one embodiment of the present invention, the temperature of the resin is about 20° C. to about 40° C. In one embodiment, the temperature is room temperature.

In one embodiment, the liquid being purified is an acetic acid or acetic anhydride feedstock. In another embodiment, the liquid being purified is an acetic acid solution, and in another embodiment, the liquid is an acetic anhydride solution, and in yet another embodiment, the liquid is a peracetic acid solution.

In one embodiment, the resin last for an extended period. In one embodiment, the resin lifetime is at least one year.

Another aspect of the present invention is a method of reducing the concentration of an iodide compound in a liquid comprising contacting the liquid with a resin, wherein the resin comprises a strong acid macroporous resin having at least 30% of the acid functional groups exchanged with silver, a dry weight capacity of at least 5.2 eq/kg, and a mean pore diameter ($D_{50}$) of about 500-800 Å, wherein the temperature of the resin is about 20° C. to about 40° C.

Another aspect of the present invention is a method of reducing the concentration of an iodide compound in a liquid comprising contacting the liquid with a resin, wherein the resin comprises a strong acid macroporous resin having at 12-25 30% of the acid functional groups exchanged with silver, a dry weight capacity of at least 5.2 eq/kg, and a mean pore diameter ($D_{50}$) of about 500-800 Å, wherein the temperature of the resin is about 20° C. to about 40° C. This method is particularly useful, in one embodiment, for iodide concentrations of greater than about 10 ppm.

Another aspect of the present invention is a method of reducing the concentration of an iodide compound in a liquid comprising contacting the liquid with a resin, wherein the resin comprises a strong acid macroporous resin having 8-12% of the acid functional groups exchanged with silver, a dry weight capacity of at least 5.2 eq/kg, and a mean pore diameter ($D_{50}$) of about 500-800 Å, wherein the temperature of the resin is about 20° C. to about 40° C. While this resin will have a shorter life cycle, it is still an aspect of the present invention and may be particularly useful in embodiments where low ppb iodides (e.g., less 10 ppm) are used since the shorter expected life cycle could tie into the plant turnaround schedule.

Another aspect of the present invention is a method of reducing the concentration of an iodide compound from an iodide-containing solution of acetic acid, acetic anhydride, or a mixture thereof comprising: contacting the liquid with a packed bed comprising an ion exchange resin, wherein the resin comprises a strong acid macroporous resin having at least 1% of the acid functional groups exchanged with silver, a dry weight capacity of at least 5.0 eq/kg, a mean pore diameter ($D_{50}$) of about 400-800 Å, a pore volume of about 0.4-0.6 ml/g, and a surface area of about 20-40 $m^2$/g; and maintaining the contact for a period of time sufficient to reduce the iodide concentration to less than 1 ppb. In one embodiment, the contacting comprises flowing the solution through a packed bed comprising the macroporous resin.

DETAILED DESCRIPTION

Macroporous Resin

Macroporous resins, such as those described by Abrams and J. R. Millar (React. Funct. Polym. 35 (1997), pp. 7-22) and in U.S. Pat. No. 4,224,415, were developed to improve kinetics by providing a highly porous copolymer bead matrix for ion exchange wherein relatively large pore sizes improves diffusion of chemical species into the interior portions of the beads (e.g., ion exchange resins, or IEX resins). Macroporous resins contain significant non-gel porosity in addition to normal gel porosity. This non-gel porosity arises from channels present between the gel lattices. These microscopic channels are separate and distinct from the micropores, which are present in all cross-linked IEX resins, as is well known to those skilled in the art. While the channels are themselves relatively small, they are large when compared with the micropores of the previously known, gel type resins. IEX resins generally have bead diameters within about 150-1,200 μm.

Various macroporous resins and methods for generating macroporosity are known in the art. The terms "macroporous," "macroreticular," "sponge-like," and "channeled" have been used, more or less interchangeably, by those skilled in the art to characterize the hazy to completely opaque beads and resins. "Pore-forming," "phase-separating," "precipitant," and "porogen"—even "diluent" less precisely—have all, likewise, been used to refer to the agent used to produce the macroporous structure. Macroporous resins having a particularly large pore diameter (e.g., 1-10 μm) have also been formed and are described in U.S. Pat. No. 6,323,249 and are exceptionally useful in applications where large species are to be isolated.

The capacity of the macroporous resin is defined as how many $H^+$ ions can be exchanged per one mass and/or volumetric unit of resin. The capacity is given as either dry weight capacity or volume capacity. The dry weight capacity is indicated as equivalents per kilogram (eq/kg) or equivalently as milliequivalents per g (meq/g) of dry resin and the volume capacity is indicated as equivalents per one liter of fully swollen resin (eq/l). The theoretical maximum dry weight capacity (one sulfone group per benzene ring for a sulfonated styrene-divinylbenzene copolymer resin) of a monosulfonated styrene-divinylbenzene copolymer resin varies between 4.8 and 5.4 eq/kg. The actual dry weight capacity for many resins is well below this maximum.

The resins of the present invention have a high dry weight capacity comparable to standard macroporous resins. In one embodiment, the dry weight capacity is at least 5.0 eq/kg. In another embodiment, the dry weight capacity is at least 5.1 eq/kg. In another embodiment, the dry weight capacity is at least 5.2 eq/kg. In another embodiment, the dry weight capacity is at least 5.3 eq/kg. In another embodiment, the dry weight capacity is at least 5.4 eq/kg.

In one embodiment, the dry weight capacity is limited to no more than 5.4 eq/kg such that the increasing capacity does not weaken the structure under sulfonation conditions.

In one embodiment, a higher dry weight capacity is derived from double sulfonation (e.g., double sulfonation on a benzene ring in a DVB-containing resin). For example, the Purolite® CT175, containing 15-20% DVB, has a 4.9 eq/kg acid capacity, and the Purolite® CT275, also containing 15-20% DVB, has a 5.2 eq/kg acid capacity. While Purolite® CT175 has the same co-polymer structure as Purolite® CT275, Purolite® CT275 is a "double sulfonated" resin, and is also called a high performance catalysts. It can be advantageous to use double sulfonated resins since, in addition to a higher dry weight acid capacity (quantity); they may also exhibit higher acidity (quality). In this embodiment, a high performance resin is used to make the silver exchange resin.

The pores created in the resins, as described herein, can have a pore diameter (e.g., pore size) ranging typically from about 100 Å to 200,000 Å (i.e., 20 μm) or higher. Preferred macroporous resins have a median pore diameter of about 400 Å to about 20,000 Å. Other preferred macroporous resins have a median pore diameter of about 400 Å to about 700 Å. The large pores of the catalysts described herein allow for reduced fouling compared to smaller pored catalysts.

The pore volume of the resin is a function of both pore size and pore density. The resin of the present invention has a pore volume of about 0.3-0.8 ml/g. In one embodiment, the pore volume is from 0.4 to 0.6 ml/g. Since pore volume is related to pore surface and pore diameter, the optimal pore volume reflects optimal surface area containing active functional groups needed for reaction kinetics. If the pore volume is too small (e.g., due to small surface and/or diameter), then the reaction may proceed too slowly (e.g., diffusion control). If the pore volume is too large, void volumes could form. Pore diameter can determine size of molecules allowed to penetrate into the resin beads. In this invention, the optimal pore diameter is important because it allows larger alkyl iodides (>C6) to access the inner active silver sites within the beads. When the alkyl group size increases, pore diameter becomes important factor in contrast to the patent (U.S. Pat. No. 6,657,078) teaching a high temperature (>50° C.) is required for removing decyl iodides and dodecyl iodides based on chosen smaller pore diameter resins.

The surface area of the resin includes both the outer surface of the resin bead and the surface of the accessible pores. Increased surface area increases the area of interaction between the resin and the solution. Preferably, the surface area is about 20-40 m$^2$/g.

The degree of cross-linking of the IEX resin is dependent on the amount of the cross-linking agent (e.g., divinylbenzene, or DVB) used during the polymerization. A macroporous resin normally comprises 4-30% divinylbenzene. In a gel resin, the DVB content is usually less than 8-10%. Thus, for macroporous resins, a range of 10-30% is preferred. Resins having a DVB concentration of from 15 to 25% are preferred in some particular embodiments of the present invention. The degree of cross-linking affects for example the mechanical strength, ion exchange capacity, water retention capacity, swelling, selectivity and chemical stability of the ion exchanger. Generally, resins with a low degree of cross-linking are soft and mechanically unstable, whereas a high degree of cross-linking generally provides hardness, fragility and increased sensitivity to osmotic effects. Resins having a lower amount of cross-linking will have more gel-like characteristics.

Resin particle size and the size distribution can also affect the behavior of an ion-exchange resin in, for example, the kinetics of mass transfer, pressure drop over a backed bed, flow channeling and the degree of packing of the bed. The mean particle size of resin or the mean sphere size (resin particles are usually spherical) refers to an average based on the volume or mass proportion of different size fractions. The sharpness of the sphere size distribution is generally described by means of a uniformity coefficient (UC). This coefficient is calculated by forming a quotient between a mesh size that retains 40% of resin particles and a mesh size retaining 90% of resin particles. This ratio is given value 1 when all the particles are of equal size. For example, a typical resin intended for water treatment has a uniformity coefficient (UC) of 1.7. The UC of industrial chromatographic separation resins varies between 1.05 and 1.25. In a preferred embodiment, the UC is between 1 and 2.

Mechanical strength describes the resin's ability to resist wearing. In a physically advantageous ion-exchange resin the particles are spherical in shape, and the resin does not comprise cracks and is not fragile. Mechanical strength may be examined, for example, by a cyclic test of watering and drying, where the resin strength is examined by subjecting the resin to repeated watering and drying operations. Physical hardness is measured by means of compression resistance. The resistance of a resin to osmotic forces is important in industrial applications. Several methods have been introduced to measure the resistance of a resin to osmotic shock. Friability, may also be measured using the Chatillon test which measures the force (grams) required to crack or fracture a resin bead when it is placed between two parallel plates. The plates are gradually brought together at a uniform rate until the bead "breakpoint" is reached. The purpose of this test is to simulate the frictional and pressure forces exerted on individual resin beads under actual use conditions.

One particular resin that can be used in the present invention is Purolite® CT275. Purolite® CT275 catalyst is a macroporous, strongly acidic, polymeric catalyst which comprises a macroporous polystyrene cross-linked with divinylbenzene having euphonic acid functional groups and a dry weight capacity of at least 5.20 eq/kg. The mean pore diameter ($D_{50}$) is 400-700 Å. Unique properties of CT275 include high acid strength, high total acid sites and higher thermal stability. This catalyst also has a unique structure with properties that include a large pore diameter and volume allowing reactants access to those active acid sites. Because of its larger pore structure, CT275 has a greater resistance to fouling due to the formation of polymeric side products. In addition, it has lower shrinking and swelling properties.

Another particular resin that can be used in the present invention is Purolite® CT276. Purolite® CT276 catalyst is also a macroporous, strongly acidic, polymeric catalyst which is similar to Purolite® CT275 but with a higher dry weight capacity (generally in the range of 5.3-5.4 eq/kg).

Formation of the Resins

The resins of the present invention can be formed by generating an interpenetrating polymeric network (IPN). One preferred macroporous resin is formed when styrene, divinylbenzene (DVB) and a porogen are mixed together with a polymerization initiator to form the monomer solution. Preferably, the DVB is present at a concentration of at least 5%. Free radical initiators are most desirable. Free radical generating compounds which may be used to effect polymerization of the monomers. In one method, the monomer phase is added to an aqueous phase for suspension polymerization of the monomers. Salt may be added to the aqueous phase to decrease the water solubility of the monomers.

Following formation of the resin, the resin can be sulfonated with sulfuric acid, oleum, sulfur trioxide, or chlorosulfonic acid to form a cation exchange resin. The resin can be made in to a high performance resin during the sulfonation process by varying the sulfonation conditions. High performance resins have a higher dry weight acid capacity and a higher acid strength than the corresponding standard acid resins.

Methods of producing ion-exchange resins from corresponding cross-linked copolymer resins are known in the art. Strongly acid cation exchangers obtained by sulfonation of cross-linked polymers, such as for example cross-linked polystyrenes are disclosed in U.S. Pat. Nos. 2,366,007, 2,466,675, 2,500,149, 2,631,127 and 2,664,801.

Formation of the Silver-Substituted Resins

Silver is exchanged with a proton of sulfuric acid at the active sites of the resin. This can be done by adding silver oxide to a solution containing the resin. The silver loading should be between 1 and 37% based on dry weight capacity. The maximum percent is theoretically limited at an maximum loading where 100% of the acid sites are exchange. This occurs, for example, at 36.4% w/w for a resin having 5.3 meq/g dry weight capacity (e.g., CT275) and at 33.6% for a resin having 4.7 meq/g dry weight capacity (e.g., A15). In one embodiment, the silver loading of the resin of the present invention is between 6 and 36% based on dry weight capacity. In another embodiment, the sliver loading is between 20 and 32% based on dry weight capacity, which is based on dry-weight resin base. Increasing the amount of silver exchanged can be used to increase the life of the silver exchange resin. However, this also increases the cost of the resin.

Iodide Removal

The macroporous resins as described herein are particularly useful for the removal of iodide compounds from a solution containing iodide compounds. This method is particularly useful for acetic acid or acetic anhydride solutions. This process generally includes feeding methanol and carbon monoxide to a carbonylation zone which contains a rhodium carbonylation catalyst, methyl iodide, an optional stabilizer such as an iodide salt, water and methyl acetate. This process is described, for example in U.S. Pat. Nos. 3,769,329; 5,001,259; and 5,416,237 and EP 0 161 874.

Reducing Iodide Concentration

The resin of the present invention is contacted with the liquid containing one or more iodide impurity.

In one embodiment, the resin is packed into a fixed bed. In another embodiment, a batch process is used.

For a fixed bed process, the liquid is preferably passed through at a predetermined rate. Feed rates are dependent on the amount of iodide impurity, the degree of purification required for the particular liquid, the temperature, and the resin used. In on embodiment, the feed rate is between 0.5 to 50 bed volumes per hour. In another embodiment, the feed rate is 5 to 15 bed volumes per hour. The resin bed may optionally be graded by back-flushing before use.

Any reasonable temperature may be used during the iodide removal process. Reasonable temperatures are those below the temperature limit for the resin (e.g., 200° C. for CT275). In one embodiment, the liquid is contacted with the resin at a temperature of between 20° C. and 80° C. In another embodiment, the liquid is contacted with the resin at a temperature of between 20° C. and 50° C. In yet another embodiment, the temperature is between 20° C. and 35° C. In one embodiment, the temperature is approximately room temperature.

The liquid may be passed through another purification bed before and/or after removal of iodide contaminants using the resin as described herein. For example, the liquid may first pass through a resin bed to remove anionic impurities including anionic iodide impurities before passing through the silver-exchange high performance resin described herein. Optionally, the liquid may be passed through two or more silver-exchange high capacity resin beds.

The level of iodide reduction is preferably to a liquid iodide concentration of less than 10 ppb (parts per billion), or more preferably less than 3 ppb. Preferably, the amount of iodide remaining after contacting the liquid with the silver-exchange high performance resin is less than 1 ppb, or more preferably less than 300 ppt (parts per trillion). Even more preferably, the resultant iodide concentration has less than 100 ppt iodide contaminant. As described herein, the iodide contaminate or impurity concentration is defined as the concentration of any molecular species containing an iodide, such as HI, $CH_3I$, $C_6H_{13}I$, $C_{10}H_{21}I$ or $C_{12}H_{25}I$ or higher carbon iodides.

In one embodiment, the iodide impurity removed according to the present invention is HI or an alkyl iodide having between 1 and 20 carbon atoms, where the alkyl iodide may be linear or branched, or optionally substituted with one or more substituent. In one embodiment, the alkyl iodide is unsubstituted. In another embodiment, the alkyl iodide has 6-20 carbon atoms. In another embodiment, the alkyl iodide has 6-12 carbon atoms. In another embodiment, the alkyl iodide has 1-12 carbon atoms. In another embodiment, the alkyl iodide has 1-8 carbon atoms. While the method as disclosed herein removes a large number of different length iodide impurities, the present invention is particularly useful for removing iodide impurities of a particular size. The larger pore size of the resins of the present invention allow for the removal of larger sized iodide compounds.

In one embodiment, the concentration of larger iodide contaminant is reduced to at least 1 ppb, or more preferably 300 ppt, or even more preferably 100 ppt. Larger iodide contaminants are those molecules containing at least one iodide and having more than 6 carbon atoms.

DEFINITIONS

The term "about" or "approximately" means within an acceptable error range for the particular value as determined by one of ordinary skill in the art, which will depend in part on how the value is measured or determined—e.g., the limitations of the measurement system, or the degree of precision required for a particular purpose. For example, "about" can mean within 1 or more than 1 standard deviations, as per the practice in the art. Alternatively, "about" can mean a range of up to 20%, preferably up to 10%, more preferably up to 5%, and more preferably still up to 1% of a given value. Where particular values are described in the application and claims, unless otherwise stated, the term "about" meaning within an acceptable error range for the particular value should be assumed.

As used herein and in the appended claims, the singular forms "a," "an," and "the," include plural referents unless the context clearly indicates otherwise. Thus, for example, reference to "a molecule" includes one or more of such molecules, "a resin" includes one or more of such different resins and reference to "the method" includes reference to equivalent steps and methods known to those of ordinary skill in the art that could be modified or substituted for the methods described herein.

As used herein, the phrase "removes contaminant" means that at least 95% of the measurable contaminant (or contaminants) is removed from the sample (e.g., a fluid stream). More preferably, at least 98% of the contaminant is removed. Even more preferably, at least 99% of the contaminant is removed, and even more preferably, at least 99.5% of the contaminant is removed. Most preferably, at least 99.9% or more of the contaminant concentration is removed.

As used herein, the terms "diameter" and "size," when referring to colloids, are both defined as the mean diameter of the colloidal particles or the mean diameter of the pore (i.e., $D_{50}$) within the colloidal particles, as appropriate.

All U.S. patents and published applications cited herein are hereby incorporated by reference.

EXAMPLES

The following examples are included to demonstrate preferred embodiments of the invention. It should be appreciated by those of skill in the art that the techniques disclosed in the examples, which follow, represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Formation of the Silver Exchange Resin

A silver exchange resin was prepared by combining Purolite® CT275 resin and silver oxide. The Purolite® CT275 resin typically has a dry weight capacity of 5.2 eq/kg. The mean size is 0.65-0.90 mm with a uniformity coefficient maximum of 1.70. The pore volume is 0.4-0.6 ml/g and the specific surface area is 20-40 m$^2$/g. The median pore diameter ($d_{50}$) is 400-700 Å. This example demonstrates formation of the silver exchange resin mono-valent silver oxide.

1000 ml of CT275 ion exchange resin, hydrogen form, was rinsed to remove any traces of chloride ion. The resin was then mixed with 915 ml of deionized water. To this slurry, 39.75 grams of Ag$_2$O was added and allowed to mix for a period of time. Acetic acid (50 ml) was added and the temperature of the slurry was increased to 52° C. for several hours. The resin was then rinsed with deionized water and transferred to a filter vessel to remove excess water and packaged. A small portion of the resin was dried and analyzed for silver content. The resin typically has silver content of 11-12% on a dried basis.

Example 2

Formation of the Silver Exchange Resins

Silver exchange resins made from three different resins were analyzed: CT275, CT145, and Amberlyst-15 (A15; Aldrich). CT145 has a dry weight capacity of 4.5 meq/g, a mean pore diameter of 350-450 Å, a pore volume of 0.2-0.3 ml/g, and a surface are of 30-35 m$^2$/g. A15 has a dry weight capacity of 4.7 meq/g, a mean pore diameter of 240-300 Å, a pore volume of 0.3-0.4 ml/g, and a surface are of 40-50 m$^2$/g. The three resins were pre-cleaned with 500 ml of 2% HCl passed through required amount of resin, washed with DI H$_2$O until free of Cl$^-$ ion, and dewatered (10 minutes on Buchman funnel). The silver uptake data was preformed at room temperature (77-78° F.) in a darkened room. The stock solution consisted of 75.7045 g of silver nitrate in an estimate of 1100 ml of DI H$_2$O. The concentration and uptake of Ag in the stock solution was determined by ICP Leeman labs Profile Plus High dispersion ICP. The ICP was standardized by using Plasma-Pure single element Ag 100.0 µg/ml at concentrations of 0, 1, 5, 10, 25, and 100 PPM. The Ag content of the stock solution was measured twice with ICP. Initially, it was 51020 ppm, while a second run provided a silver content of 40410 ppm. This second value is more consistent with the amount of silver nitrate added into the stock solution. The 40,410 ppm also agrees better with the uptake data.

The final loading was determined by allowing the resin to sit in the stock Ag solution overnight, washing the resin with 500 ml of DI H$_2$O, and dewatering for ten minutes. The dewatered resin (≈1.8 g) was than digested with 5 ml of H$_2$SO$_4$ and peroxide, and diluting to a known volume. The diluted digested resin solution was tested for Ag on a Perkins Elmer Analyst 100, which was standardized with the ICP's Ag standards of 1, 5, 10, and 25 ppm.

Moistures were determined by an oven method 12 hours @ 110° F., to determine amount of weight loss.

Example 3

Silver Uptake Result

The silver uptake of the three resins formed in Example 2 was measured to obtain the Kppm Ag in the solution during the uptake into the resin. Each of the resins obtained steady state within 500 seconds to provide a final silver concentration of 17.6 Kppm Ag (CT145), 16.0 Kppm Ag (A15) and 15.5 Kppm Ag (CT275). The silver uptake of the resin was also measured as a percent of the resin dry weight (w/w). Similarly, the dry weight capacity for each of the silver exchange resins was measured. These values are:

| Catalyst | CT275 | CT145 | A15 |
|---|---|---|---|
| Silver uptake % Ag Dry wt. (w/w) | 36.64 | 33.31 | 31.94 |
| Dry weight capacity (meq/g) | 5.26 | 5.08 | 4.7 |

Thus, the CT275 resin is found to have a higher dry weight acid capacity (high performance catalyst) than the CT145 and A15 resins. In fact, the dry weight capacity for CT275 under the loading conditions described herein is essentially equivalent to the maximum loading (100% exchange acid sites provides 36.36% based on dry weight basis). CT275 can load more silver through the exchange mechanism than other standard catalysts such as A15, CT145, etc and is thus particularly preferred. This higher loading of silver of CT275 can help increase the catalyst life.

Example 4

Iodide Concentrations

The silver-loaded CT275 (CT275Ag) was used in a high speed study for the removal of two different sized iodides. This study was performed at 45° C. and at either 40 bed volumes per hr. or 6 bed volumes per hr. in a fixed bed reactor. The total iodides for a sample initially containing 200 ppb pentyl iodide and a sample initially containing 200 ppb dodecyl iodide were tested. The iodide content are:

|  | | Iodide effluent concentration | | |
|---|---|---|---|---|
|  | Iodide conc. in Feed | CT275Ag | CT169Ag | CT145Ag |
| C$_5$H$_{11}$I @ 40 BV Total Iodides | 200 ppb | 3.2 ppb | 4.1 ppb | 7.5 ppb |
| C$_{12}$H$_{25}$I @ 6 BV Total Iodides | 200 ppb | 0.59 ppb | 3.1 ppb | 3.3 ppb |

Thus, the resin can be used to remove both short and long chain iodide contaminants at 45° C.

This experiment also demonstrates that CT275Ag works well under a high flow rate conditions (40 bed volume per hr.).

What is claimed is:

1. A method of reducing the concentration of an iodide compound in a liquid comprising contacting the liquid with a resin, wherein the resin comprises a strong acid macroporous resin
    having at least 1% of the acid functional groups exchanged with silver,
    a dry weight capacity of at least 5.0 eq/kg,
    a mean pore diameter (D$_{50}$) of about 400-800 Å,
    a pore volume of about 0.4-0.6 ml/g, and
    a surface area of about 20-40 m$^2$/g.

2. The method of claim 1, wherein the resin has a volume capacity of at least 1.40 eq/l.

3. The method of claim 1, wherein the resin has a dry weight capacity is at least 5.1 eq/kg.

4. The method of claim 3, wherein the resin has a dry weight capacity is at least 5.3 eq/kg.

5. The method of claim 1, wherein the resin has a mean pore diameter ($D_{50}$) of at least 500 Å.

6. The method of claim 1, wherein the resin has a mean pore diameter ($D_{50}$) of about 500-700 Å.

7. The method of claim 1, wherein the silver loading is between 1 and 36% based on dry-weight resin base.

8. The method of claim 7, wherein the silver loading is between 8 and 25% based on dry-weight resin base.

9. The method of claim 1, wherein the resin polymer comprises approximately 70-92% polystyrene and approximately 8-30% divinylbenzene.

10. The method of claim 9, wherein the resin polymer comprises approximately 75-85% polystyrene and approximately 15-25% divinylbenzene.

11. The method of claim 1, wherein the iodide compound is one or more of a $C_1$-$C_{12}$ alkyl.

12. The method of claim 1, wherein the concentration of the iodide compounds is reduced to less than about 1 ppb.

13. The method of claim 12, wherein the concentration of the iodide compounds is reduced to less than about 100 ppt.

14. The method of claim 1, wherein contacting comprises flowing the liquid through a packed bed comprising the macroporous resin.

15. The method of claim 14, wherein a flow rate is 5 to 15 bed volumes per hour.

16. The method of claim 1, wherein the temperature of the resin is about 20° C. to about 40° C.

17. The method of claim 1, wherein the solution is an acetic acid or acetic anhydride feedstock.

18. The method of claim 1, wherein the liquid is an acetic acid solution, an acetic anhydride solution, or a peracetic acid solution.

19. The method of claim 1, wherein the resin lifetime is at least one year.

20. The method of claim 1, wherein the strong acid macroporous resin has at least 50% of the acid functional groups exchanged with silver,
    a dry weight capacity of at least 5.2 eq/kg, and
    a mean pore diameter ($D_{50}$) of about 500-800 Å.
    wherein the temperature of the resin is about 20° C. to about 40° C.

21. A method of reducing the concentration of an iodide compound from an iodide-containing solution of acetic acid, acetic anhydride, or a mixture thereof comprising:
    contacting the liquid with a packed bed comprising an ion exchange resin, wherein the resin comprises a strong acid macroporous resin
        having at least 1% of the acid functional groups exchanged with silver,
        a dry weight capacity of at least 5.0 eq/kg,
        a mean pore diameter ($D_{50}$) of about 400-800 Å,
        a pore volume of about 0.4-0.6 ml/g, and
        a surface area of about 20-40 $m^2$/g; and
    maintaining the contact for a period of time sufficient to reduce the iodide concentration to less than 1 ppb.

22. The method of claim 21, wherein contacting comprises flowing the solution through a packed bed comprising the macroporous resin.

* * * * *